United States Patent
Frühauf

(10) Patent No.: US 10,707,836 B2
(45) Date of Patent: Jul. 7, 2020

(54) ESTIMATION OF HARMONIC FREQUENCIES FOR HEARING IMPLANT SOUND CODING USING ACTIVE CONTOUR MODELS

(71) Applicant: MED-EL Elektromedizinische Geraete GmbH, Innsbruck (AT)

(72) Inventor: Florian Frühauf, Rinn (AT)

(73) Assignee: MED-EL Elektromedizinische Geraete GmbH, Innsbruck (AT)

(*) Notice: Subject to any disclaimer, the term of this patent is extended or adjusted under 35 U.S.C. 154(b) by 118 days.

(21) Appl. No.: 15/765,746

(22) PCT Filed: Oct. 7, 2016

(86) PCT No.: PCT/US2016/055885
§ 371 (c)(1),
(2) Date: Apr. 4, 2018

(87) PCT Pub. No.: WO2017/062701
PCT Pub. Date: Apr. 13, 2017

(65) Prior Publication Data
US 2018/0287590 A1    Oct. 4, 2018

Related U.S. Application Data

(60) Provisional application No. 62/239,305, filed on Oct. 9, 2015.

(51) Int. Cl.
*H03H 17/02* (2006.01)
*A61N 1/36* (2006.01)
(Continued)

(52) U.S. Cl.
CPC ..... *H03H 17/0223* (2013.01); *A61N 1/36039* (2017.08); *A61N 1/3727* (2013.01);
(Continued)

(58) Field of Classification Search
CPC .......... H03H 17/0223; H03H 17/0219; H03H 17/0213; A61N 1/3727; A61N 1/36039; A61N 1/0541
See application file for complete search history.

(56) References Cited

U.S. PATENT DOCUMENTS 7,561,709 B2    7/2009    Vandali et al.
2009/0024183 A1    1/2009    Fitchmun
(Continued)

FOREIGN PATENT DOCUMENTS

EP    2 826 521 A1    1/2015
WO    WO 2004/043537 A1    5/2004
(Continued)

OTHER PUBLICATIONS

Aubert et al., "Image segmentation using active contours: calculus of variations or shape gradients?," SIAM Journal on Applied Mathematics, vol. 63, No. 6, pp. 2128-2154, 2003.
(Continued)

*Primary Examiner* — Mark Bockelman
(74) *Attorney, Agent, or Firm* — Sunstein LLP

(57) ABSTRACT

A signal processing arrangement generates electrical stimulation signals to electrode contacts in an implanted cochlear implant array. An input sound signal is processed to generate band pass signals that each represent an associated band of audio frequencies. A spectrogram representative of frequency spectrum present in the input sound signal is generated. A characteristic envelope signal is produced for each band pass signal based on its amplitude. An active contour model is applied to estimate dominant frequencies present in the spectrogram, and the estimate is used to generate stimulation timing signals for the input sound signal. The elec-
(Continued)

trode stimulation signals are produced for each electrode contact based on the envelope signals and the stimulation timing signals.

12 Claims, 9 Drawing Sheets

(51) Int. Cl.
  *A61N 1/372* (2006.01)
  *A61N 1/05* (2006.01)
(52) U.S. Cl.
  CPC .... *H03H 17/0213* (2013.01); *H03H 17/0219* (2013.01); *A61N 1/0541* (2013.01)

(56) References Cited

U.S. PATENT DOCUMENTS

| | | |
|---|---|---|
| 2010/0185261 A1 | 7/2010 | Schleich |
| 2010/0191309 A1 | 7/2010 | Schleich |
| 2010/0198300 A1 | 8/2010 | Smith |
| 2012/0004706 A1 | 1/2012 | Meister et al. |
| 2012/0209351 A1 | 8/2012 | Meister et al. |
| 2012/0303093 A1 | 11/2012 | Wouters et al. |
| 2014/0058478 A1 | 2/2014 | Frühauf et al. |
| 2015/0088225 A1 | 3/2015 | Noble et al. |
| 2015/0163604 A1 | 6/2015 | Frühauf et al. |
| 2015/0163605 A1 | 6/2015 | Meister et al. |

FOREIGN PATENT DOCUMENTS

| | | | |
|---|---|---|---|
| WO | WO 2010/085477 A1 | 7/2010 | |
| WO | WO 2015/026690 A1 | 2/2015 | |
| WO | WO 2015/042091 A1 | 3/2015 | |
| WO | WO 2017/070138 A1 | 4/2017 | |

OTHER PUBLICATIONS

Blake et al., "Active Contours: The Application of Techniques from Graphics, Vision, Control, Theory and Statistics to Visual Tracking of Shapes in Motion," Secaucus, USA: Springer-Verlag, 1998.

Frühauf et al., "Experiments and Algorthims to Detect Snow Avalanche Victims Using Airborne Ground-Penetrating Radar," IEEE Transactions on Geoscience and Remote Sensing, vol. 47, issue 7, pp. 2240-2251, Jul. 2009.

Gerhard, "Pitch Extraction and Fundamental Frequency: History and Current Techniques," Technical Report TR-CS Jun. 2003, 23 pages, Nov. 2003.

International Searching Authority, International Search Report—International Application No. PCT/US16/55885, dated Dec. 23, 2016 together with the Written Opinion of the International Searching Authority, 15 pages.

International Searching Authority, International Search Report—International Application No. PCT/US2016/57585, dated Dec. 23, 2016 together with the Written Opinion of the International Searching Authority, 15 pages.

Kass et al., "Snakes: Active contour models," International Journal of Computer Vision, vol. 1, No. 4, pp. 321-331, 1988.

Majdak et al., "Effects of interaural time differences in fine structure and envelope on lateral discrimination in electric hearing," Journal of the Acoustical Society of America, vol. 120, No. 4, pp. 2190-2201, Oct. 2006.

Vandali et al., "Pitch ranking ability of cochlear implant recipients: A comparison of sound-processing strategies," Journal of the Acoustical Society of America, vol. 117, No. 5, pp. 3126-3138, May 2005.

Vermeire et al., "Better Speech Recognition in Noise with the Fine Structure Processing Coding Strategy," ORL; Journal for Oto-Rhino-Laryngology and Its Related Specialties, vol. 72, pp. 305-311, 2010.

European Patent Office, Extended European Search Report, Application No. 16854379.1, dated Mar. 25, 2019, 7 pages.

ESTIMATION OF HARMONIC FREQUENCIES FOR HEARING IMPLANT SOUND CODING USING ACTIVE CONTOUR MODELS

This application is a national phase entry of Patent Cooperation Treaty Application PCT/US16/55885, filed Oct. 7, 2016, which in turn claims priority from U.S. Provisional Patent Application 62/239,305, filed Oct. 9, 2015, both of which are incorporated herein by reference in their entireties.

FIELD OF THE INVENTION

The present invention relates to hearing implant systems, and more specifically, to techniques for producing electrical stimulation signals in such systems.

BACKGROUND ART

A normal ear transmits sounds as shown in FIG. 1 through the outer ear 101 to the tympanic membrane 102, which moves the bones of the middle ear 103 (malleus, incus, and stapes) that vibrate the oval window and round window openings of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses which are transmitted to the cochlear nerve 113, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid may be used to provide mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

FIG. 1 also shows some components of a typical cochlear implant system, including an external microphone that provides an audio signal input to an external signal processor 111 where various signal processing schemes can be implemented. The processed signal is then converted into a digital data format, such as a sequence of data frames, for transmission into the implant 108. Besides receiving the processed audio information, the implant 108 also performs additional signal processing such as error correction, pulse formation, etc., and produces a stimulation pattern (based on the extracted audio information) that is sent through an electrode lead 109 to an implanted electrode array 110.

Typically, the electrode array 110 includes multiple electrode contacts 112 on its surface that provide selective stimulation of the cochlea 104. Depending on context, the electrode contacts 112 are also referred to as electrode channels. In cochlear implants today, a relatively small number of electrode channels are each associated with relatively broad frequency bands, with each electrode contact 112 addressing a group of neurons with an electric stimulation pulse having a charge that is derived from the instantaneous amplitude of the signal envelope within that frequency band.

It is well-known in the field that electric stimulation at different locations within the cochlea produce different frequency percepts. The underlying mechanism in normal acoustic hearing is referred to as the tonotopic principle. In cochlear implant users, the tonotopic organization of the cochlea has been extensively investigated; for example, see Vermeire et al., *Neural tonotopy in cochlear implants: An evaluation in unilateral cochlear implant patients with unilateral deafness and tinnitus,* Hear Res, 245(1-2), 2008 Sep. 12 p. 98-106; and Schatzer et al., *Electric-acoustic pitch comparisons in single-sided-deaf cochlear implant users: Frequency-place functions and rate pitch,* Hear Res, 309, 2014 March, p. 26-35 (both of which are incorporated herein by reference in their entireties).

In some stimulation signal coding strategies, stimulation pulses are applied at a constant rate across all electrode channels, whereas in other coding strategies, stimulation pulses are applied at a channel-specific rate. Various specific signal processing schemes can be implemented to produce the electrical stimulation signals. Signal processing approaches that are well-known in the field of cochlear implants include continuous interleaved sampling (CIS), channel specific sampling sequences (CSSS) (as described in U.S. Pat. No. 6,348,070, incorporated herein by reference), spectral peak (SPEAK), and compressed analog (CA) processing.

In the CIS strategy, the signal processor only uses the band pass signal envelopes for further processing, i.e., they contain the entire stimulation information. For each electrode channel, the signal envelope is represented as a sequence of biphasic pulses at a constant repetition rate. A characteristic feature of CIS is that the stimulation rate is equal for all electrode channels and there is no relation to the center frequencies of the individual channels. It is intended that the pulse repetition rate is not a temporal cue for the patient (i.e., it should be sufficiently high so that the patient does not perceive tones with a frequency equal to the pulse repetition rate). The pulse repetition rate is usually chosen at greater than twice the bandwidth of the envelope signals (based on the Nyquist theorem).

In a CIS system, the stimulation pulses are applied in a strictly non-overlapping sequence. Thus, as a typical CIS-feature, only one electrode channel is active at a time and the overall stimulation rate is comparatively high. For example, assuming an overall stimulation rate of 18 kpps and a 12 channel filter bank, the stimulation rate per channel is 1.5 kpps. Such a stimulation rate per channel usually is sufficient for adequate temporal representation of the envelope signal. The maximum overall stimulation rate is limited by the minimum phase duration per pulse. The phase duration cannot be arbitrarily short because, the shorter the pulses, the higher the current amplitudes have to be to elicit action potentials in neurons, and current amplitudes are limited for various practical reasons. For an overall stimulation rate of 18 kpps, the phase duration is 27 µs, which is near the lower limit.

The Fine Structure Processing (FSP) strategy by Med-El uses CIS in higher frequency channels, and uses fine structure information present in the band pass signals in the lower frequency, more apical electrode channels. In the FSP electrode channels, the zero crossings of the band pass filtered time signals are tracked, and at each negative to positive zero crossing, a Channel Specific Sampling Sequence (CSSS) is started. Typically CSSS sequences are applied on up to 3 of the most apical electrode channels, covering the frequency range up to 200 or 330 Hz. The FSP arrangement is described further in Hochmair I, Nopp P, Jolly C, Schmidt M, Schößer H, Garnham C, Anderson I, *MED-EL Cochlear Implants: State of the Art and a Glimpse into the Future*, Trends in Amplification, vol. 10, 201-219, 2006, which is incorporated herein by reference. The FS4 coding strategy differs from FSP in that up to 4 apical channels can have their fine structure information used. In FS4-p, stimulation pulse sequences can be delivered in parallel on any 2 of the 4 FSP electrode channels. With the FSP and FS4 coding strategies, the fine structure information is the instantaneous frequency information of a given electrode channel, which may provide users with an improved hearing sensation, better speech understanding and enhanced perceptual audio quality. See, e.g., U.S. Pat. No. 7,561,709; Lorens et al. "Fine structure processing improves speech perception as well as objective and subjective benefits in pediatric MED-EL COMBI 40+ users." *International journal of pediatric otorhinolaryngology* 74.12 (2010): 1372-1378; and Vermeire et al., "Better speech recognition in noise with the fine structure processing coding strategy." *ORL* 72.6 (2010): 305-311; all of which are incorporated herein by reference in their entireties.

Many cochlear implant coding strategies use what is referred to as an n-of-m approach where only some number n electrode channels with the greatest amplitude are stimulated in a given sampling time frame. If, for a given time frame, the amplitude of a specific electrode channel remains higher than the amplitudes of other channels, then that channel will be selected for the whole time frame. Subsequently, the number of electrode channels that are available for coding information is reduced by one, which results in a clustering of stimulation pulses. Thus, fewer electrode channels are available for coding important temporal and spectral properties of the sound signal such as speech onset.

In addition to the specific processing and coding approaches discussed above, different specific pulse stimulation modes are possible to deliver the stimulation pulses with specific electrodes—i.e. mono-polar, bi-polar, tri-polar, multi-polar, and phased-array stimulation. And there also are different stimulation pulse shapes—i.e. biphasic, symmetric triphasic, asymmetric triphasic pulses, or asymmetric pulse shapes. These various pulse stimulation modes and pulse shapes each provide different benefits; for example, higher tonotopic selectivity, smaller electrical thresholds, higher electric dynamic range, less unwanted side-effects such as facial nerve stimulation, etc.

Fine structure coding strategies such as FSP and FS4 use the zero-crossings of the band-pass signals to start a channel-specific sampling sequence (CSSS) pulse sequences for delivery to the corresponding electrode contact. Zero-crossings reflect the dominant instantaneous frequency quite robustly in the absence of other spectral components. But in the presence of higher harmonics and noise, problems can arise. See, e.g., WO 2010/085477 and Gerhard, David, *Pitch extraction and fundamental frequency: History and current techniques*. Regina: Department of Computer Science, University of Regina, 2003; both incorporated herein by reference in their entireties.

FIG. 2 shows a sample spectrogram for a sample of clean speech including estimated instantaneous frequencies for Channels 1 and 3 as reflected by evaluating the signal zero-crossings. The horizontal black dashed lines show the channel frequency boundaries—Channels 1, 2, 3 and 4 range between 100, 198, 325, 491 and 710 Hz, respectively. It can be seen in FIG. 2 that during periods of a single dominant harmonic in a given frequency channel, the estimate of the instantaneous frequency is smooth and robust; for example, in Channel 1 from 1.6 to 1.9 seconds, or in Channel 3 from 3.4 to 3.5 seconds. When additional frequency harmonics are present in a given channel, or when the channel signal intensity is low, the instantaneous frequency estimation becomes inaccurate, and, in particular, the estimated instantaneous frequency may even leave the frequency range of the channel.

Gerhard 2003 cited above gives an overview of algorithms that can be used to estimate the fundamental frequency. These algorithms include time-domain methods, frequency-domain methods and statistical frequency-domain methods. Most of them are computationally too expensive to be usable in real life and/or cannot guarantee robustness. Vandali et al. "Pitch ranking ability of cochlear implant recipients: A comparison of sound-processing strategies." *The Journal of the Acoustical Society of America* 117.5 (2005): 3126-3138 (incorporated herein by reference in its entirety) uses positive peaks instead of the zero-crossings to preserve the fine structure information. But peak detection has the same problems as the zero-crossings technique when more than one harmonic and/or noise occurs in a given frequency channel.

In WO 2010/085477, the filter bank resolution is enhanced to resolve the low frequency harmonics. As a result, the estimation of the instantaneous frequency is robust when using the zero-crossing approach. A signal-dependent algorithm also is used to select channels of the high-resolution bands, which are then sent to the implant.

In [I82_2013], the dominant frequency in a channel is estimated by skipping to fast zero-crossing. The time differences of the residual zero-crossing are inverted and smoothed to get an estimation of the dominant frequency.

SUMMARY OF THE INVENTION

Embodiments of the present invention are directed to a signal processing arrangement and corresponding method that generates electrode stimulation signals to electrode contacts in an implanted cochlear implant array. An input sound signal is processed to generate band pass signals that each represent an associated band of audio frequencies. A spectrogram representative of frequency spectrum present in the input sound signal is generated. A characteristic envelope signal is produced for each band pass signal based on its amplitude. An active contour model is applied to estimate dominant frequencies present in the spectrogram, and the estimate is used to generate stimulation timing signals for the input sound signal. The electrode stimulation signals are produced for each electrode contact based on the envelope signals and the stimulation timing signals.

In further specific embodiments, the spectrogram may be generated using a short time Fourier transformation (STFT). The electrode stimulation signals may include channel-specific sampling sequences (CSSS). Using the estimate of dominant frequencies may include smoothing the spectrogram, and the estimate of dominant frequencies may include a determination of one or more harmonic frequencies present in the spectrogram. Typically, the method may be iteratively repeated over a period of time intervals.

BRIEF DESCRIPTION OF THE DRAWINGS

The file of this patent contains at least one photograph. Copies of this patent with photograph will be provided by the Office upon request and payment of the necessary fee.

DETAILED DESCRIPTION OF SPECIFIC EMBODIMENTS

The bandwidths of the band pass filters in a typical cochlear implant signal processor are quite large compared to the auditory filters in normal hearing, and there is likely to be more than one frequency harmonic in each electrode channel. This can cause a poor estimation of the instantaneous frequency of the dominant harmonic in a given channel.

Aubert, Gilles, et al. "Image segmentation using active contours: Calculus of variations or shape gradients?." *SIAM Journal on Applied Mathematics* 63.6 (2003): 2128-2154 (incorporated herein by reference in its entirety) describes active contour models to segment parts of image frames out of a video.

Fruehauf, Florian, et al. "Experiments and algorithms to detect snow avalanche victims using airborne ground-penetrating radar." *Geoscience and Remote Sensing, IEEE Transactions on* 47.7 (2009): 2240-2251.(incorporated herein by reference in its entirety) describes using an active contour model to segment the snow layer out of radar data to automatically detect avalanche victims by flying with a helicopter over an avalanche and using a radar antenna mounted on the helicopter that receives the radar data. The amount of data is very large and the evaluation must be available in real time, but still the snow layer can be extracted out of the radar data.

Embodiments of the present invention are based on applying an active contour model to a spectrogram of the input sound signal, and using that to estimate the course of dominant frequencies such as the dominant harmonics. This estimation is then independent of the cochlear implant filter bank. Such embodiments may provide improved speech intelligibility and perception of music and pitch in hearing implant systems.

Figure 1:
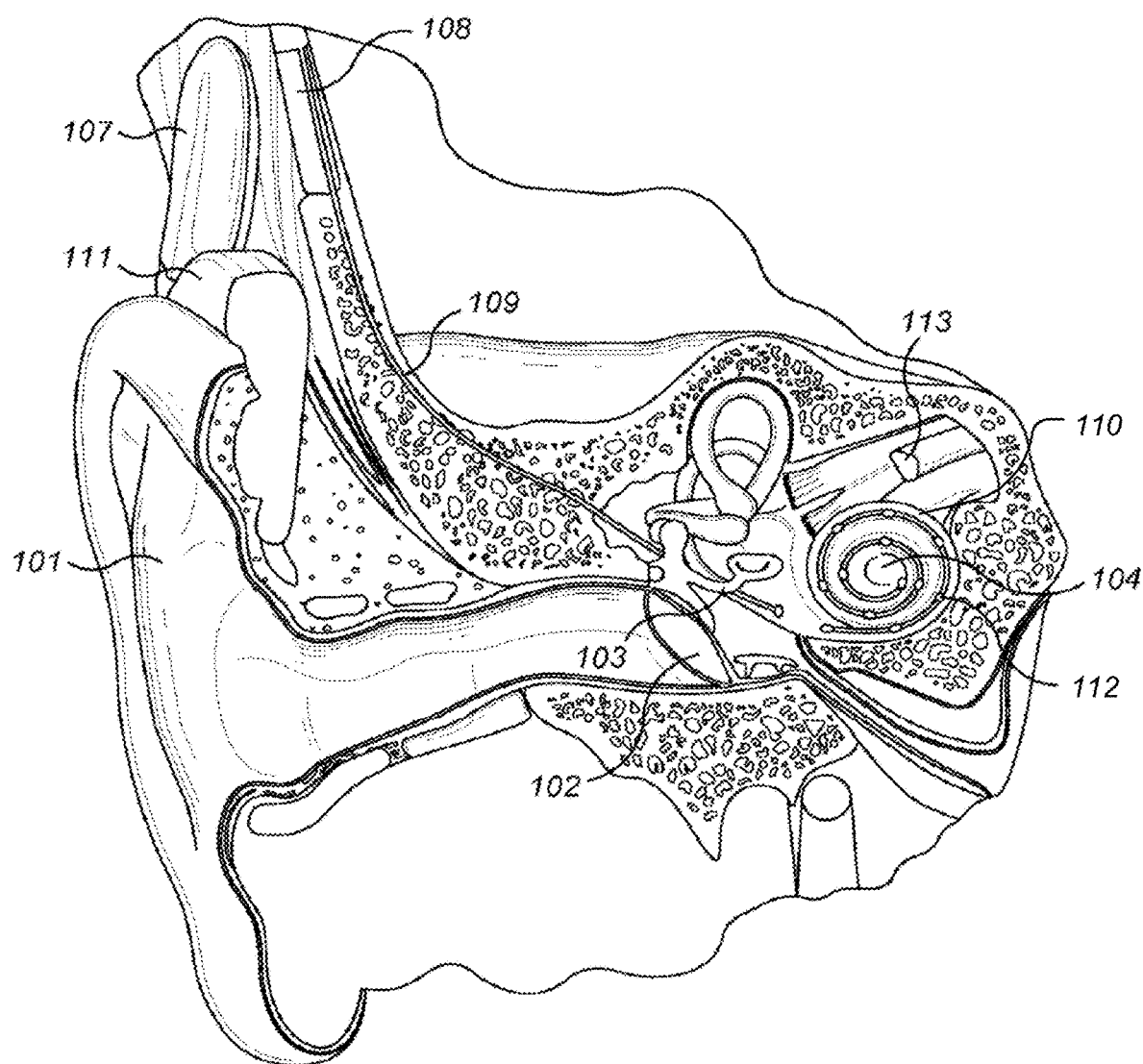
FIG. 1 shows a section view of a human ear with a typical cochlear implant system designed to deliver electrical stimulation to the inner ear.
Figure 2:
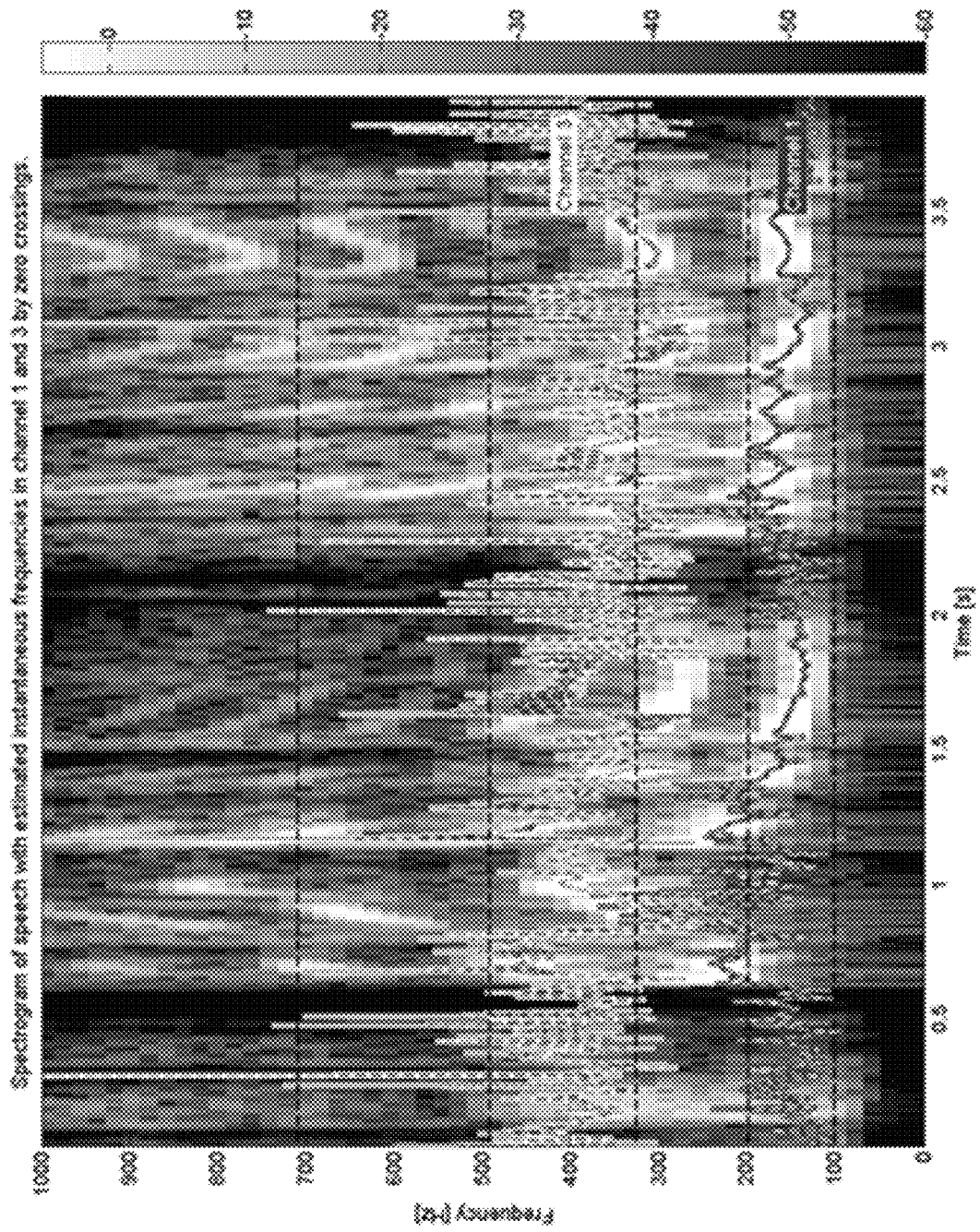
FIG. 2 shows a sample spectrogram for a sample of clean speech including estimated instantaneous frequencies for Channels 1 and 3 based on zero-crossings.
Figure 3:
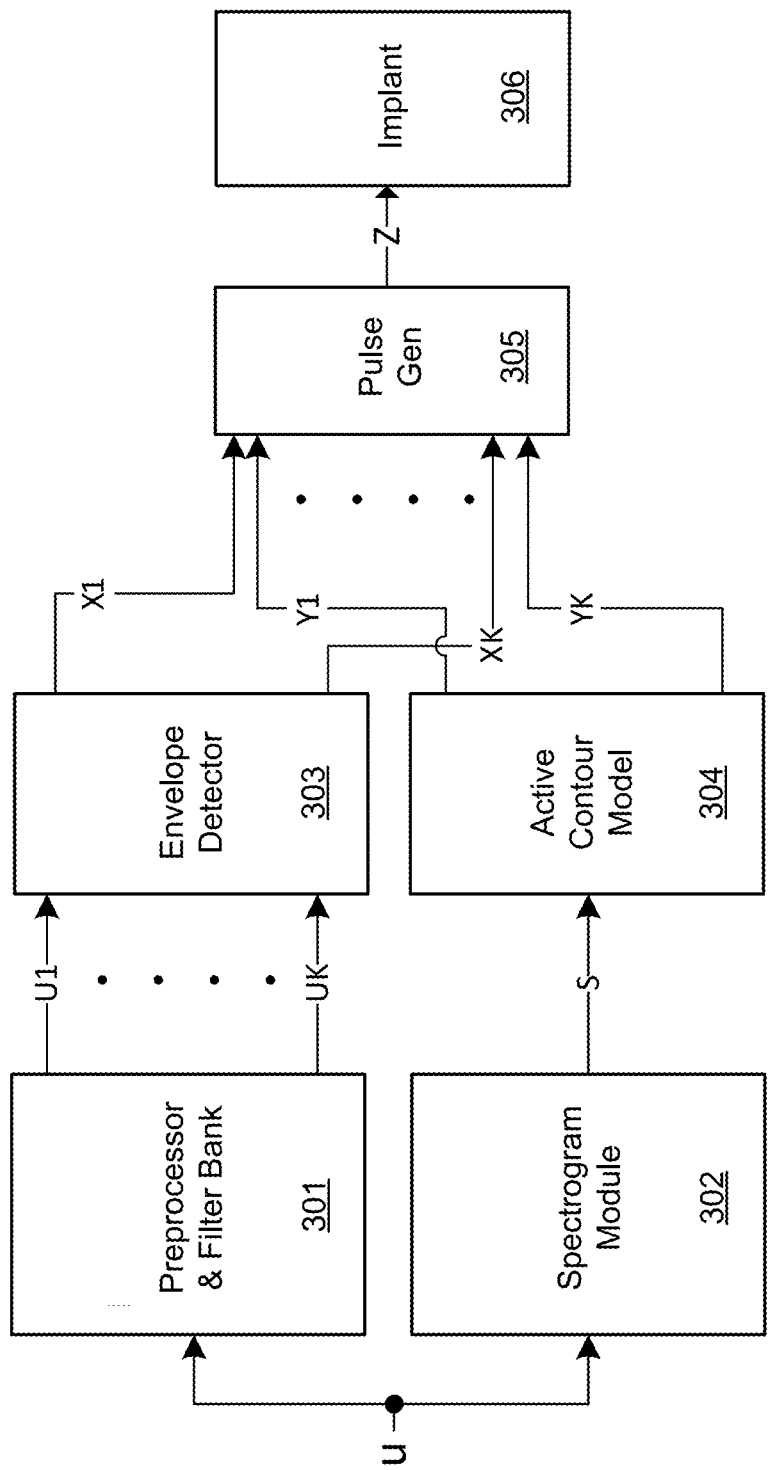
FIG. 3 shows various functional blocks in a signal processing arrangement for a hearing implant according to an embodiment of the present invention.
Figure 4:
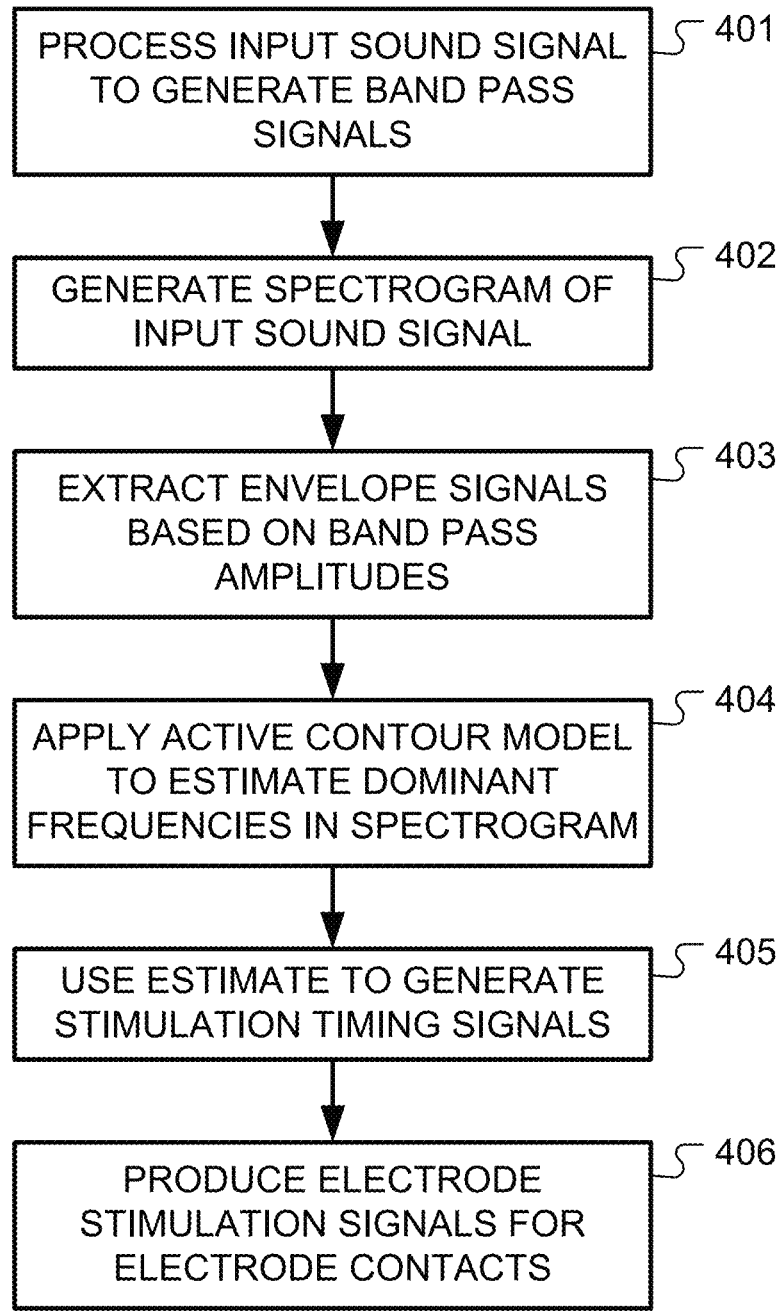
FIG. 4 shows various logical steps in developing electrode stimulation signals according to an embodiment of the present invention.

FIG. 3 shows various functional blocks in a signal processing arrangement for a hearing implant and FIG. 4 is a flow chart showing various logical steps in producing electrode stimulation signals to electrode contacts in an implanted cochlear implant array according to an embodiment of the present invention. A pseudo code example of such a method can be set forth as:

```
Input Signal Preprocessing:
    BandPassFilter (input_sound, band_pass_signals)
Spectrogram:
    Spectrogram (input_sound, spectrogram)
Envelope Extraction:
    BandPassEnvelope (band_pass_signals, band_pass_envelopes)
Active Contour Model:
    DominantFrequencies (spectrogram, dom_freqs)
    StimulationTiming (dom_freqs, stim_timing)
Pulse Generation:
    PulseGenerate (band_pass_envelopes, stim_timing, out_pulses)
```

The details of such an arrangement are set forth in the following discussion.

In the arrangement shown in FIG. 3, the initial input sound signal is produced by one or more sensing microphones, which may be omnidirectional and/or directional. Combined Preprocessor and Filter Bank 301 pre-processes this input sound signal u, step 401, with a bank of multiple parallel band pass filters, each of which is associated with a specific band of audio frequencies; for example, using a filter bank with 12 digital Butterworth band pass filters of 6th order, Infinite Impulse Response (IIR) type, so that the input sound signal is filtered into some K band pass signals, $U_1$ to $U_K$ where each signal corresponds to the band of frequencies for one of the band pass filters. Each output of the sufficiently narrow CIS band pass filters for a voiced speech input signal may roughly be regarded as a sinusoid at the center frequency of the band pass filter which is modulated by the envelope signal. This is also due to the quality factor ($Q \approx 3$) of the filters. In case of a voiced speech segment, this envelope is approximately periodic, and the repetition rate is equal to the pitch frequency. Alternatively and without limitation, the Preprocessor Filter Bank 301 may be implemented based on use of a fast Fourier transform (FFT) or a short-time Fourier transform (STFT). Based on the tonotopic organization of the cochlea, each electrode contact in the scala tympani typically is associated with a specific band pass filter of the combined Preprocessor and Filter Bank 301. The combined Preprocessor and Filter Bank 301 also may perform other initial signal processing functions such as for example automatic gain control (AGC) and/or noise reduction and/or wind noise reduction and/or beamforming and other well-known signal enhancement functions. It is understood that instead of the combined Preprocessor and Filter Bank 301, the Preprocessor and Filter Bank may be separate. In this embodiment the Preprocessor may process input sound signal u and the preprocessed output signal is subsequently used for input and processing by Filter Bank and Spectrogram Module 302.

Figure 5:
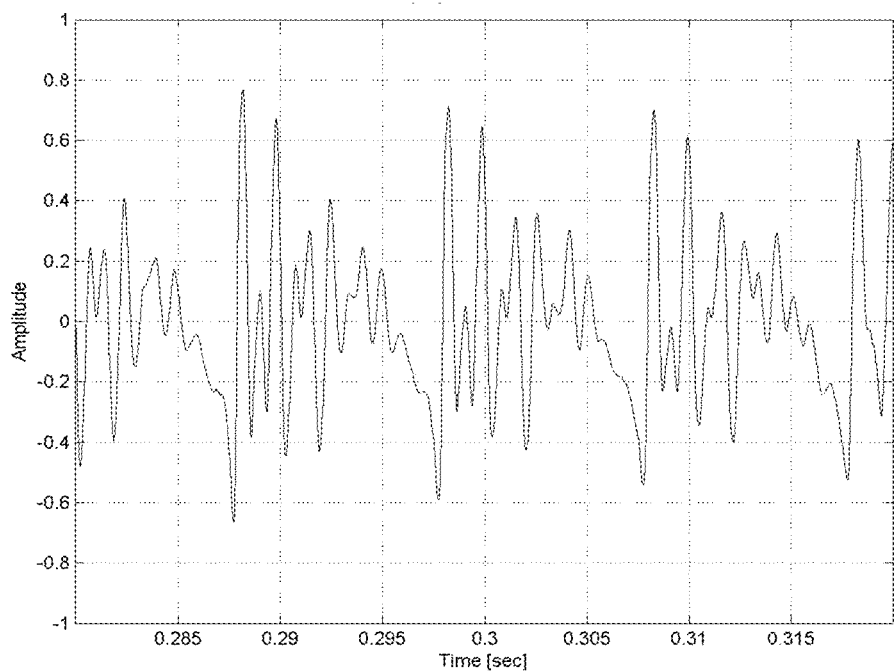
FIG. 5 shows an example of a short time period of an audio speech signal from a microphone.
Figure 6:
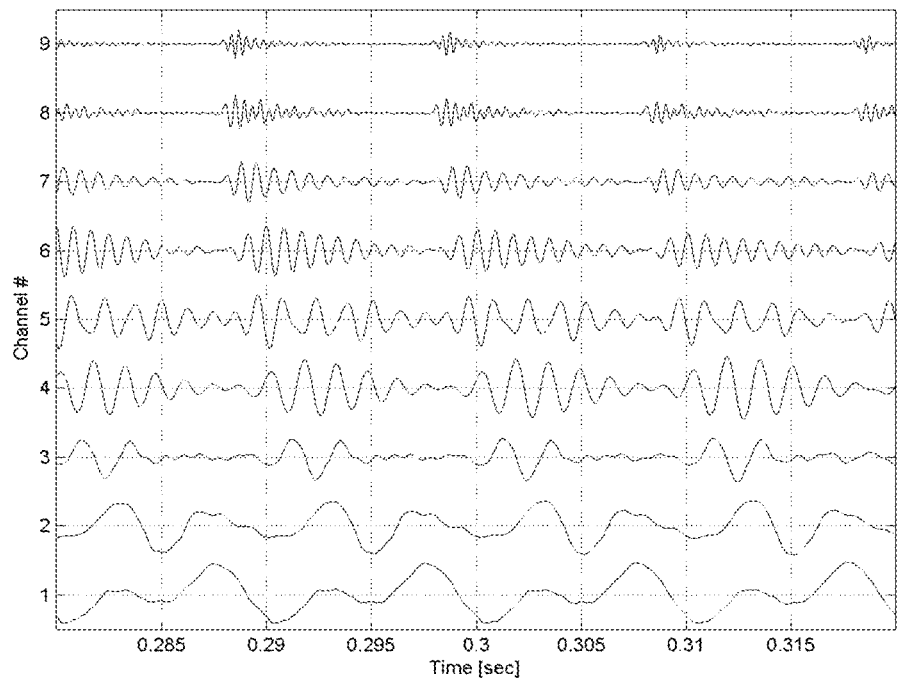
FIG. 6 shows an acoustic microphone signal decomposed by band-pass filtering by a bank of filters into a set of band pass signals.

FIG. 5 shows an example of a short time period of an input sound signal u from a sensing microphone, and FIG. 6 shows the microphone signal decomposed by band-pass filtering by a bank of filters. An example of pseudocode for an infinite impulse response (IIR) filter bank based on a direct form II transposed structure is given by Fontaine et al., *Brian Hears: Online Auditory Processing Using Vectorization Over Channels*, Frontiers in Neuroinformatics, 2011; incorporated herein by reference in its entirety.

The band pass signals $U_1$ to $U_K$ (which can also be thought of as electrode channels) are output to an Envelope Detector 303, which extracts characteristic envelope signals outputs $X_1, \ldots, X_K$, step 403, that represent the channel-specific band pass envelopes. The envelope extraction can be represented by $X_k = LP(|U_k|)$, where |.| denotes the absolute value and LP (.) is a low-pass filter; for example, using 12 rectifiers and 12 digital Butterworth low pass filters of 2nd order, IIR-type. Alternatively, the Envelope Detector 303 may extract the Hilbert envelope, if the band pass signals $U_1, \ldots, U_K$ are generated by orthogonal filters.

Figure 7:
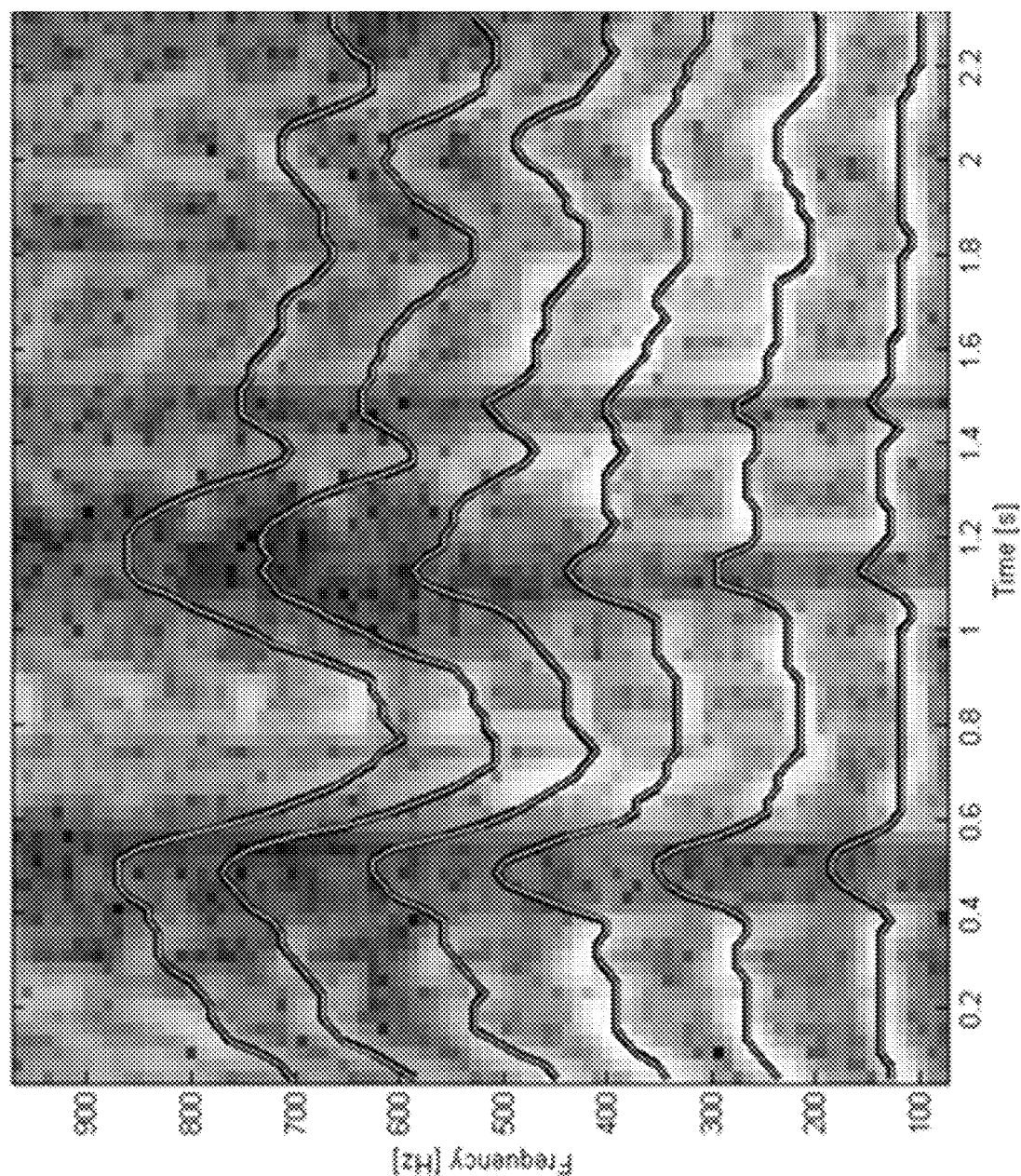
FIG. 7 shows a spectrogram of a clean speech input sound signal with estimated harmonics.

A Spectrogram Module 302 generates a spectrogram S representative frequency spectrum present in the input sound signal u, step 402; for example by using a short time Fourier transformation (STFT). FIG. 7 shows a spectrogram S(f, t) for a clean speech input sound signal u, where the first and second dimension refers to the frequency f and time t, respectively, and where the estimated harmonic frequencies are shown by the black-white-black lines. The $k^{th}$ harmonic is given through a function $$h_k : \begin{cases} T \to F \\ t \to h_k(t) \end{cases},$$

which assigns each time $t \in T$ to a frequency $h_k(t) \in F$. A timing signal $Y_k(t)$ can be obtained by $$Y_k(t) = \begin{cases} 1 & t = t_k[n+1] = t_k[n] + \dfrac{1}{h_k(t_k[n])} \\ 0 & \text{otherwise} \end{cases}.$$

Then the time differences $t_k[n+1] - t_k[n]$ of the ones in $Y_k$ correlate with the estimated frequency of the $k^{th}$ harmonic.

The spectrogram S then is the input signal for an Active Contour Model Module 304, which applies an active contour model to the spectrogram S, step 404. This may be generally as based on the use of active contour models as described in the prior art as to image processing, embodiments of the present invention represent the first use of such active contour model-based image processing techniques to the processing of input sound signals for a hearing implant. The Active Contour Model Module 304 then uses the estimate of the dominant frequencies present in the spectrogram S to generate stimulation timing signals, step 405.

The extracted signal envelopes $X_1, \ldots, X_K$ from the Envelope Detector 303, and the stimulation timing signals $Y_1, \ldots, Y_K$ from the Active Contour Model Module 304 are input signals to a Pulse Generator 305 that produces the electrode stimulation signals Z for the electrode contacts in the implanted electrode array of the Implant 306, step 406. The Pulse Generator 305 applies a patient-specific mapping function—for example, using instantaneous nonlinear compression of the envelope signal (map law)—That is adapted to the needs of the individual cochlear implant user during fitting of the implant in order to achieve natural loudness growth. The Pulse Generator 305 may apply logarithmic function with a form-factor C as a loudness mapping function, which typically is identical across all the band pass analysis channels. In different systems, different specific loudness mapping functions other than a logarithmic function may be used, with just one identical function is applied to all channels or one individual function for each channel to produce the electrode stimulation signals. The electrode stimulation signals typically are a set of symmetrical biphasic current pulses.

Returning to describe in greater detail the operation of the Active Contour Model Module 304, the spectrogram S can be treated as a continuous mapping from $F \times T \in \mathbb{R}_+^2 \to \mathbb{R}_+$, where $\mathbb{R}_+$ denotes the positive real numbers. First, the Active Contour Model Module 304 smooths the spectrogram S for robustness reasons: $\Psi_1(f, t) = S(f, t) + \eta \cdot \Delta_f S(f,t)$, where $\Delta_f$ is the Laplace operator corresponding to the frequency and $\eta > 0$. This smoothing corresponds to solving a one dimensional heat equation with initial condition S up to time $\eta$. $\eta$ is a parameter and determines the smoothing. The larger $\eta$ is chosen, the stronger the smoothing will be.

Figure 8A:
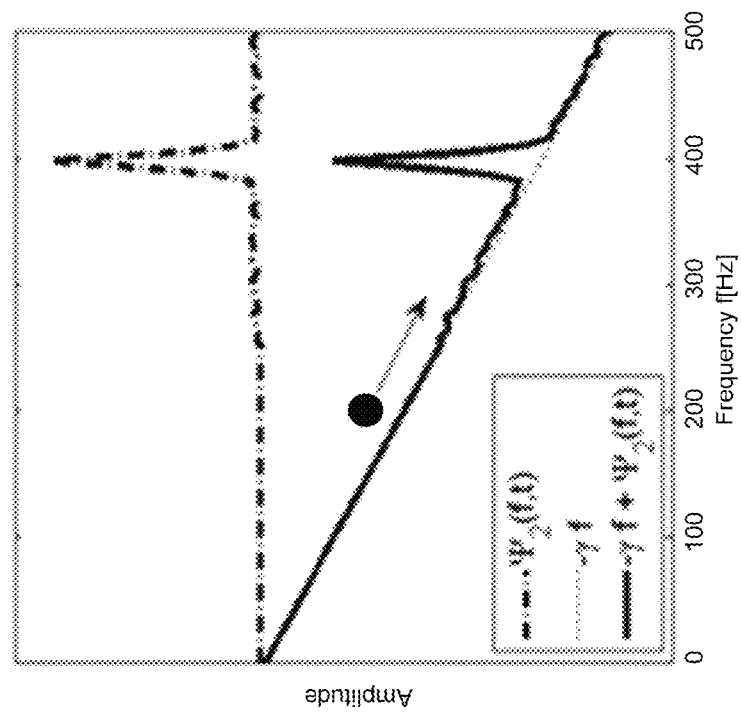
FIG. 8A-8B shows the principle of an active contour model.

Then the Active Contour Model Module 304 can detect the first harmonic present in the spectrograms S, given $p_{1,t}: f \mapsto -\gamma f + \Psi_1(f, t)$ be a potential for fixed t and $\gamma > 0$. FIG. 8A shows a plot of $p_{1,t}$ where the peaks of $\Psi$ at 200 and 400 Hz correspond to the first two harmonics, and the Active Contour Model Module 304 finds the first local minima of $p_{1,t}$, which is indicated in the plot by the rolling ball. The first found local minimum is denoted by $h_1(t)$. Then the Active Contour Model Module 304 finds the second harmonic. Since the second harmonic has a higher frequency than $h_1(t)$, then:

$$\Psi_2(f, t) = \begin{cases} 0 & \text{for } f \le h_1(t) + \delta \\ \Psi_1(f, t) & \text{for } f > h_1(t) + \delta \end{cases}.$$

Figure 8B:
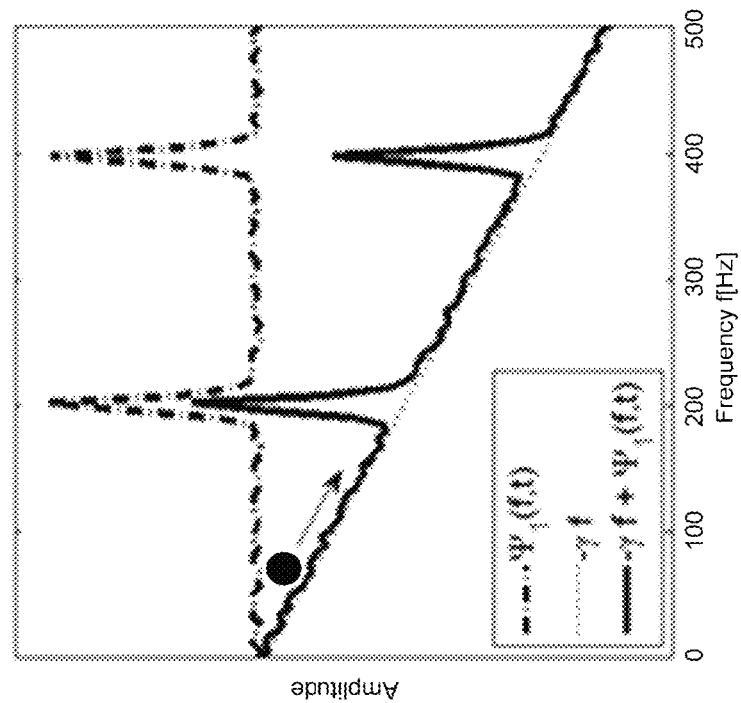

FIG. 8B shows the potential $p_{2,t}$ where $\Psi_1$ is replaced by $\Psi_2$. By choosing an appropriate $\delta$, the first harmonic is neglected in $\Psi_2$ and the second harmonic is given by the first local minimum $h_2(t)$ of $p_{2,t}$. The Active Contour Model Module 304 then repeats the calculation for $k = 3, 4, \ldots,$ to estimate the higher harmonics, getting $h_k$ by replacing $h_1$, $p_{2,t}$, $\Psi_1$ and $\Psi_2$ through $h_{k-1}$, $p_{k,t}$, $\Psi_{k-1}$ and $\Psi_k$, respectively.

The foregoing uses only the information for a single moment in time, so that a single false estimation can occur and the estimated harmonics then will not be smooth, and during speech pauses, the course of the estimation will become erratic. To avoid that, the calculations can be iteratively repeated over a period of time intervals. Consider the function:

$$H_k(h) = \int_{t_1}^{t_2} p_{k,t}(h(t))dt + \frac{\alpha}{2}\int_{t_1}^{t_2} h'(t)^2 dt,$$

where h'(t) denotes the derivative with respect to time. The $k^{th}$ harmonic can be chosen as the local minimizer $h_k$ of $H_k$. The first term of $H_k$ forces $h_k$ to be in the first local minimum, while the second term makes $h_k$ smooth. The parameter $\alpha$ controls the influence of the two terms. The calculation of the minimizer can be done, for example, by a steepest descent method where the corresponding Euler Lagrange equation must be solved:

$$\frac{\partial H_k}{\partial h} - \frac{\partial}{\partial t}\frac{\partial H_k}{\partial h'} = -\gamma + \frac{\partial \Psi_k(h(t), t)}{\partial f} - \alpha h''(t) = 0.$$

This is done iteratively by $$h_{k,i+1}(t) = h_{k,i}(t) + d \cdot \left(\gamma - \frac{\partial \Psi_k(h_{k,i}(t), t)}{\partial f} + \alpha h''_{k,i}(t)\right)$$

with step size d.

Based on those considerations, the following implementation is yielded in a discrete setting where the spectrogram S and $\Psi_k$ are given as a matrix: S: $\{f_1, \ldots, f_M\} \times \{t_1, \ldots, t_N\} \to \mathbb{R}_+$:

1. Define a rounding operator: $\lfloor f \rfloor = \operatorname{argmin}_{\{f_1, \ldots, f_M\}} |f - f_k|$.
2. Calculate: $\Psi_1(f_m, t_n) = S(f_m, t_n) + \eta \cdot (S(f_{m-1}, t_n) - 2S(f_m, t_n) + S(f_{m+1}, t_n))$ for $n = 1, \ldots, N$. Set $k=1$, $h_{k,1}(t_n) = f_1$ and $g_1(t_n) = 0$ for $n = 1, \ldots, N$, and choose an appropriate stopping threshold parameter $g > 0$.
3. Set $i=1$ and $\Omega = \{1, \ldots, N\}$.
4. Calculate for $n = 1, \ldots, N$.
   a. If $n \in \Omega$:

i. $h''_{k,i}(t_n) = h_{k,i}(t_{n-1}) - 2h_{k,i}(t_n) + h_{k,i}(t_{n+1})$.

ii. $g_{i+1}(t_n) = g_i(t_n) + \dfrac{\partial \Psi_k(h_{k,i}(t_n), t_n)}{\partial f}$ $= g_i(t_n) + \dfrac{\Psi_k(\lfloor h_{k,i}(t_n) \rfloor, t_n) - \Psi_k(\lfloor h_{k,1}(t_n) \rfloor, t_n)}{h_{k,i}(t_n) - h_{k,1}(t_n)}$ iii. $h_{k,i+1}(t_n) = h_{k,i}(t_n) + d \cdot (\gamma - g_{i+1}(t_n) + \alpha h''_{k,i}(t_n))$.

b. Otherwise, $h_{k,i+1}(t_n) = h_{k,i}(t_n)$.
5. Check a stopping criteria for $n \in \Omega$.
   a. If $g_{i+1}(t_n) > g$, set $\Omega = \Omega \setminus \{n\}$.
   b. If $h_{k,i+1}(t_n) > f_M$ or $h_{k,i+1}(t_n) < f_1$, set $\Omega = \Omega \setminus \{n\}$ and $h_{k,i+1}(t_n) = h_{k,i}(t_n)$.
   c. If $\Omega = \emptyset$ go to step 7.
6. Set $i = i+1$ and go to step 4.
7. Set the k.th harmonic $h_k = h_{k,i+1}$. If k is equal the number of wanted harmonics, then stop.
8. Initialization for the next harmonic: For all $(f, t) \in \{f_1, \ldots, f_M\} \times \{t_1, \ldots, t_N\}$ let $$\Psi_{k+1}(f, t) = \begin{cases} 0 & \text{for } f \leq h_k(t) + \delta \\ \Psi_k(f, t) & \text{for } f > h_k(t) + \delta \end{cases}, g_1(t) = 0 \text{ and } h_{k+1,1}(t) = h_k(t) + \delta.$$

Go to step 3.

Figure 9:
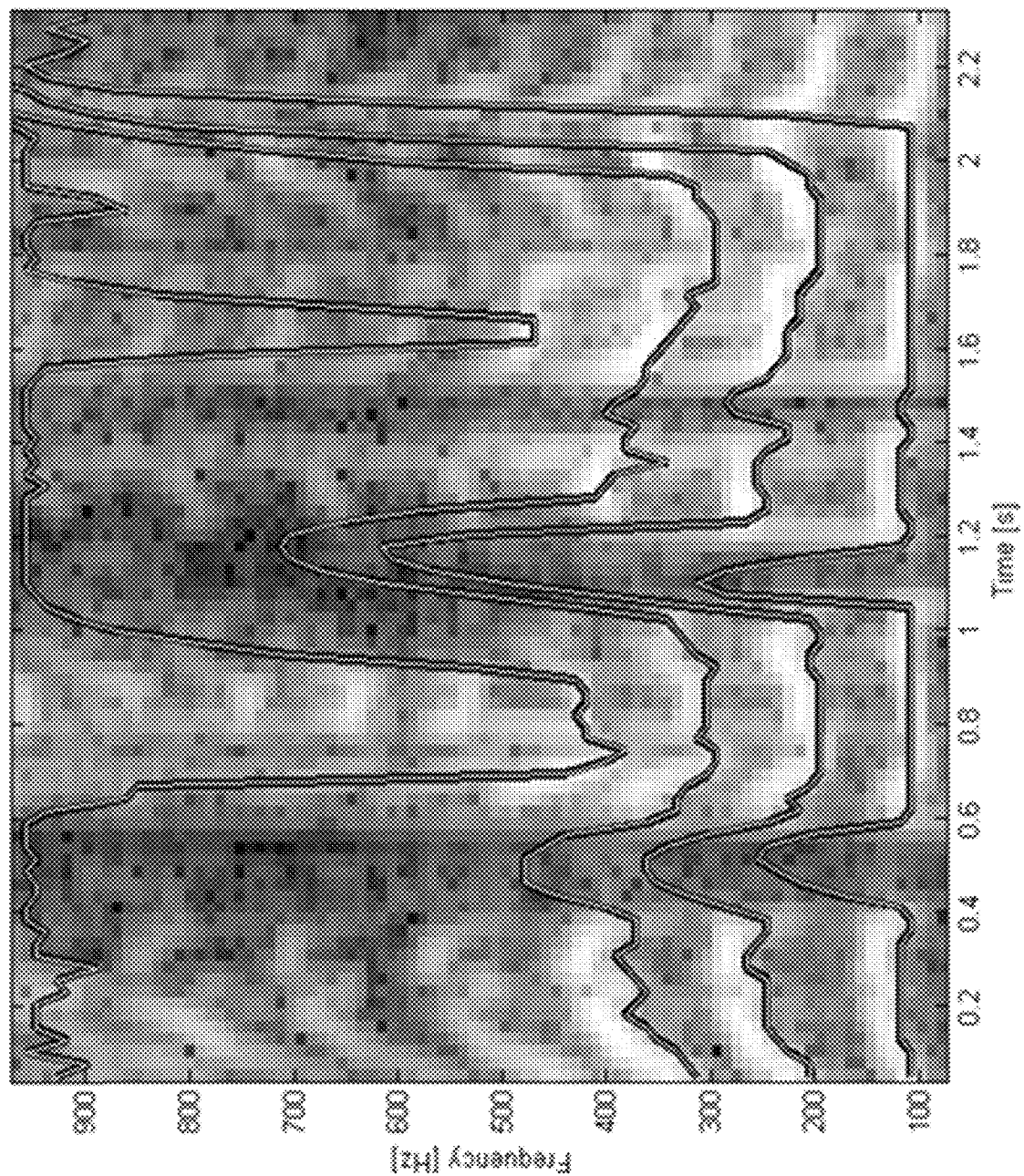
FIG. 9 shows another spectrogram of a clean speech input sound signal with estimated harmonics.

FIG. 9 shows an example from such an implementation where the spectrogram S has a frequency resolution from 78-966 Hz with a step size of ~10Hz. The time resolution is given by 0 to 2.3 seconds with step size ~51 msec. The estimation of the first three harmonics is good during the speech phases, but the calculated values are too small since the algorithm is designed to stop at the first local minimum of the potentials $p_{k,t}$. To avoid such stopping in the local minima, the term $$\dfrac{\Psi_k(\lfloor h_{k,i}(t_n) \rfloor, t_n) - \Psi_k(\lfloor h_{k,1}(t_n) \rfloor, t_n)}{h_{k,i}(t_n) - h_{k,1}(t_n)}$$

can be exchanged by $$\sum_{\substack{f \in [f_1, \ldots, f_M] \\ f \leq h_{k,i}(t_n)}} \Psi_k(f, t_n)$$

in 4.a.ii. of the above implementation. This yields for $h_{k,i}(t_n) = f_i$ that $g_i(t_n)$ is the cumulative sum of $\Psi_k(\cdot, t_n)$. Thus, the stopping criteria 5.a. above is reached at a high value of $\Psi_k(\cdot, t_n)$. Furthermore, a factor also can be introduced into the calculation of $\Psi_k$ in step 8 since the harmonic amplitudes generally decrease. Thus $$\Psi_{k+1}(f, t) = \begin{cases} 0 & \text{for } f \leq h_k(t) + \delta \\ \beta \cdot \Psi_k(f, t) & \text{for } f > h_k(t) + \delta \end{cases} \text{ with } \beta_k \geq 1.$$

In FIG. 7, the result of this modified implementation is shown where it can be seen that the first six harmonics are well estimated.

Figure 10:
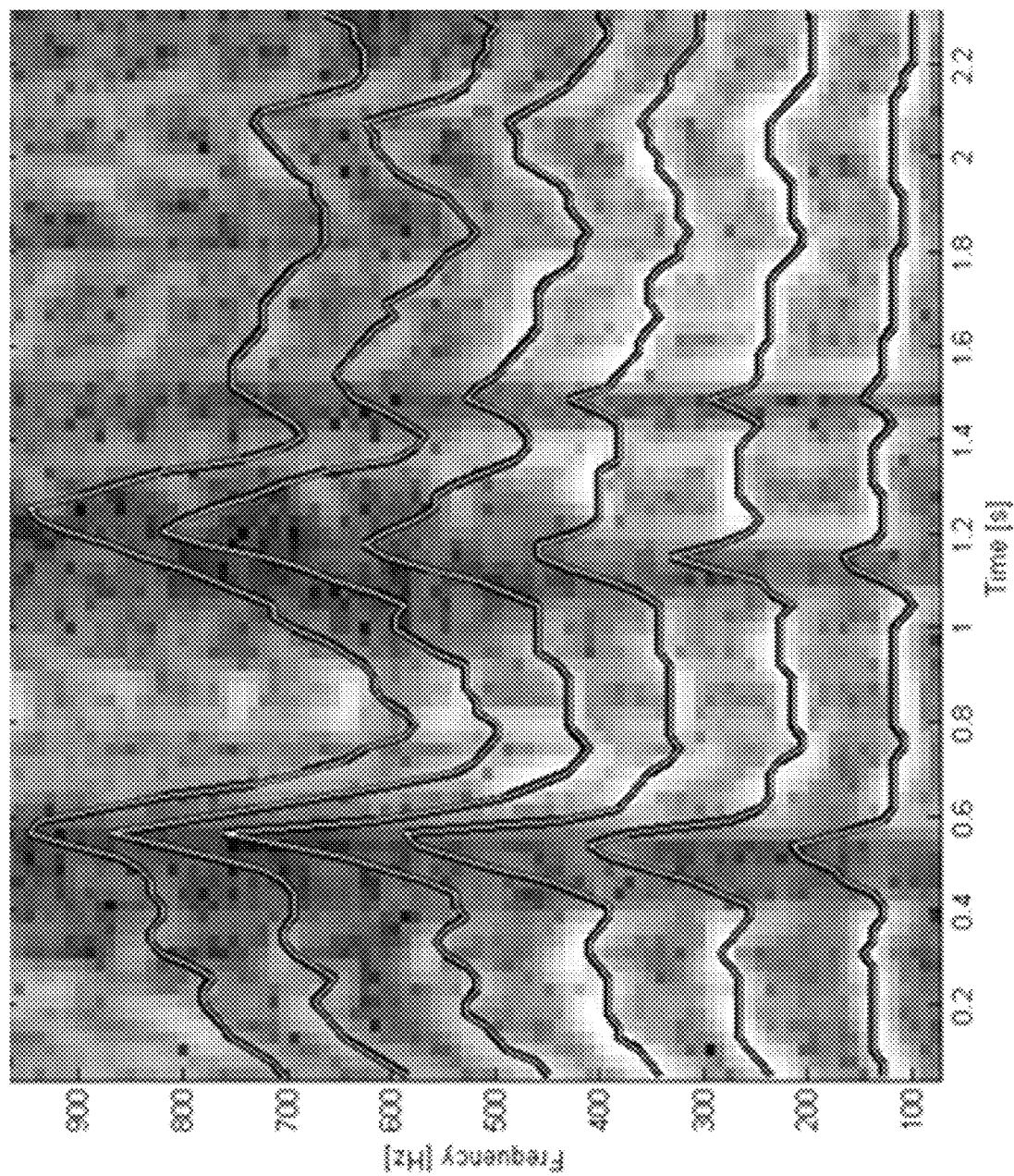
FIG. 10 shows a spectrogram of a clean speech input sound signal with modified estimated harmonics according to an embodiment of the present invention.

Considering an actual in a hearing implant speech processor, the spectrogram S can be divided into segments in time: $S_{l,L}: \{f_1, \ldots, f_M\} \times \{t_{l+1}, \ldots, t_{L+1}\} \to \mathbb{R}_+$ with $S_{l,L}(\cdot, t_j) = S(\cdot, t_{j+1})$ for $j = 1, \ldots, L$. Then the modified implementation just discussed can be applied to each $S_{l,L}$ and achieve the harmonics $h_k^l$ for $l = 0, \ldots, N-L$. Setting $h_k(t_j) = h_k^0(t_j)$ for $j = 0, \ldots, L$ (initialization) and for the following segments, using only the last value: $h_k(t_{L+l}) = h_k^l(t_{L+l})$ for $l = 1, \ldots, N-L$. The resultant harmonics are shown in FIG. 10 where the estimations are comparable to the results in FIG. 7.

Various refinements or modifications alone or in combination are possible in different specific embodiments, including:

Other methods can be used to get the spectrogram S; for example, applying an STFT on the band pass signals $U_1, \ldots, U_K$.

The calculation of the stimulation timing signals $Y_k$ can be changed.

The approach of the active contour model can be changed; for example, using another smoothing term $\int_{t_1}^{t_2} h'(t)^2 dt$ or potential function.

The calculation of $\Psi_k$ also can be modified.

The calculation of the envelope signals can be modified to be a function of the spectrogram: $(X_1, \ldots, X_K) = F(S)$.

The calculation of the envelope signals can be modified to be a function of the spectrogram and the estimated harmonics and/or the timing signals.

The input signal of the generation of the spectrogram S can be modified; for example, though Preprocessor that for example may pre-process the input sound signal with automatic gain control and/or noise reduction functions.

Harmonics have the property that $f_k = k \cdot f_0$ with fundamental frequency $f_0$. This information of harmonics can be introduced into the active contour model, for example by adding the additional term $$\dfrac{\alpha_2}{2} \int_{t_1}^{t_2} \left( \sum_{j=1}^{k} \left( h(t) - \dfrac{k}{j} h_{j-1}(t) \right)^2 \right)$$

into the functional $H_k$.

The information of the estimated harmonics can also be used in noise reduction and/or a classification algorithm to improve the signal-processing in these modules.

Applying an active contour model to estimate dominant frequencies present in a spectrogram of the input sound signal can further lead to the development of new coding strategies concepts where the actual harmonics determine the starting points of a CSSS and/or the psychoacoustic phenomenon of the phantom fundamental can be exploited.

The course of the dominant frequencies that is determined could also be useful in a scene classification algorithm, and the acquired classification could then be used to control further signal processing. For example a stationary noise reduction (NR) could be turned off when listening to music, or a beamformer could be turned on in a conversation with loud surrounding background noise. The knowledge of the dominant frequencies can be used in a NR as information for a voice-activity detector, which might be able to distinguish between speech and other sounds based on the harmonics present in speech.

Embodiments of the invention may be implemented in part in any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method for generating electrode stimulation signals for electrode contacts in an implanted cochlear implant electrode array, the method comprising:
    processing an input sound signal to generate a plurality of band pass signals, each band pass signal representing an associated band of audio frequencies and having a characteristic amplitude;
    generating a spectrogram representative of frequency spectrum present in the input sound signal;
    extracting a characteristic envelope signal for each band pass signal based on its amplitude;
    applying an active contour model to estimate dominant frequencies present in the spectrogram;
    using the estimate of dominant frequencies to generate stimulation timing signals for the input sound signal; and
    producing the electrode stimulation signals for each electrode contact based on the envelope signals and the stimulation timing signals
    stimulating the auditory nerve tissue with the electrode contacts using the electrode stimulation signals.

2. The method according to claim 1, wherein the spectrogram is generated using a short time Fourier transformation (STFT).

3. The method according to claim 1, wherein the electrode stimulation signals include channel-specific sampling sequences (CSSS).

4. The method according to claim 1, wherein using the estimate of dominant frequencies includes smoothing the spectrogram.

5. The method according to claim 1, wherein the estimate of dominant frequencies includes a determination of one or more harmonic frequencies present in the spectrogram.

6. The method according to claim 1, wherein the method is iteratively repeated over a period of time intervals.

7. A system for generating electrode stimulation signals of a cochlear implant to electrode contacts in an implantable cochlear implant electrode array, the system comprising:
    an implantable electrode array having a plurality of electrode contacts;
    a preprocessor filter bank configured to process an input sound signal to generate a plurality of band pass signals, each band pass signal representing an associated band of audio frequencies and having a characteristic amplitude;
    a spectrogram module configured to generate a spectrogram representative of frequency spectrum present in the input sound signal;
    an envelope detector configured to extract a characteristic envelope signal for each band pass signal based on its amplitude;
    an active contour model module configured to:
        i. apply an active contour model to the spectrogram to estimate dominant frequencies present in the spectrogram, and
        ii. using the estimate of dominant frequencies to generate stimulation timing signals for the input sound signal; and
    a pulse generator configured to produce and apply the electrode stimulation signals to each electrode contact so as to stimulate the auditory nerve tissue, the electrode stimulation signals based on the envelope signals and the stimulation timing signals.

8. The system according to claim 7, wherein the spectrogram module is configured to use a short time Fourier transformation (STFT) to generate the spectrogram.

9. The system according to claim 7, wherein the active contour model module is configured to use Channel-Specific Sampling Sequences (CSSS) to generate the stimulation timing signals.

10. The system according to claim 7, wherein the active contour model module is configured to include in the estimate of dominant frequencies a smoothing of the spectrogram.

11. The system according to claim 7, wherein the active contour model module is configured to include in the estimate of dominant frequencies a determination of one or more harmonic frequencies present in the spectrogram.

12. The system according to claim 7, wherein the system is configured to iteratively repeat the processing of the input sound signal over a period of time intervals.

* * * * *